United States Patent [19]
Lee et al.

[11] Patent Number: 5,265,608
[45] Date of Patent: Nov. 30, 1993

[54] STEROID ELUTING ELECTRODE FOR PERIPHERAL NERVE STIMULATION

[75] Inventors: Philip Lee, Woodbury; Kenneth Stokes, Brooklyn Park; Michael Colson, Minneapolis, all of Minn.

[73] Assignee: Medtronic, Inc., Minneapolis, Minn.

[21] Appl. No.: 802,953

[22] Filed: Dec. 5, 1991

Related U.S. Application Data

[63] Continuation-in-part of Ser. No. 483,455, Feb. 22, 1990, Pat. No. 5,092,332.

[51] Int. Cl.$^5$ .......................... A61B 5/04; A61N 1/05
[52] U.S. Cl. .................................. 128/642; 607/118
[58] Field of Search .................. 128/642, 784–786, 128/419 C, 419 P

[56] References Cited

U.S. PATENT DOCUMENTS

| | | | |
|---|---|---|---|
| H356 | 11/1987 | Stokes et al. | 128/785 |
| 1,662,446 | 3/1928 | Wappler . | |
| 3,421,511 | 1/1969 | Schwartz | 128/419 |
| 3,654,933 | 4/1972 | Hagfors | 128/419 |
| 3,724,467 | 4/1973 | Avery et al. | 128/784 |
| 3,822,708 | 7/1974 | Zilber | 128/784 |
| 3,957,036 | 5/1976 | Normann | 128/642 |
| 4,281,668 | 8/1981 | Richter et al. | 128/784 |
| 4,341,221 | 7/1982 | Testerman | 128/642 |
| 4,506,680 | 3/1985 | Stokes | 128/786 |
| 4,573,481 | 4/1986 | Bullara | 128/784 |
| 4,577,642 | 3/1986 | Stokes | 128/784 |
| 4,602,624 | 7/1986 | Naples et al. | 128/784 |
| 4,606,118 | 8/1986 | Cannon | 29/825 |
| 4,711,251 | 12/1987 | Stokes | 128/784 |
| 4,735,208 | 4/1988 | Wyler et al. | 128/642 |
| 5,095,905 | 3/1992 | Klepinski | 128/784 X |
| 5,103,837 | 4/1992 | Weidlich et al. | 128/784 |

OTHER PUBLICATIONS

Scientific Program from the *3rd Internal Symposium on Transformed Skeletal Muscle for Cardiac Assist and Repair*. This conference was held in Canada from Sep. 29 to Oct. 2, 1988.
Lee et al. "Threshold And Impedance . . . Cuff Electrodes", Jan. 24, 1990.

*Primary Examiner*—Lee S. Cohen
*Attorney, Agent, or Firm*—Harold R. Patton; Gregory P. Gadson

[57] ABSTRACT

An improved electrode for establishing electrical contact with a nerve of a patient. This electrical contact may be used to sense neural activity on the nerve or to artificially stimulate it to perform various medical treatments. One embodiment of the electrode has an outer cuff of an insulating material which is sutured around the nerve to be contacted. A drug impregnated layer of material is positioned inside of the outer cuff. This material is a polymeric matrix which permits the drug to leach out at a predetermined rate. The drug is preferably a glucocortico steroid such as dexamethasone sodium phosphate. The actual electrical contact is produced by metallic foil which is positioned on the surface of the drug impregnated layer of material which is located inside of the cuff. A second embodiment employs a half cuff which is held in contact with the nerve tissue by being sutured to muscle tissue. The insulative substrate of the half cuff is a drug impregnated polymeric matrix. The electrode is a metallic disc, preferably round or oval in shape, which is recessed into the insulative substrate. An insulated lead electrically couples the metallic foil or metallic disc to an electronic circuit located remote from the nerve. The leaching out of the drug serves to control inflammation, irritation and swelling, and stabilizes the impedance and threshold of the nerve/electrode interface.

3 Claims, 4 Drawing Sheets

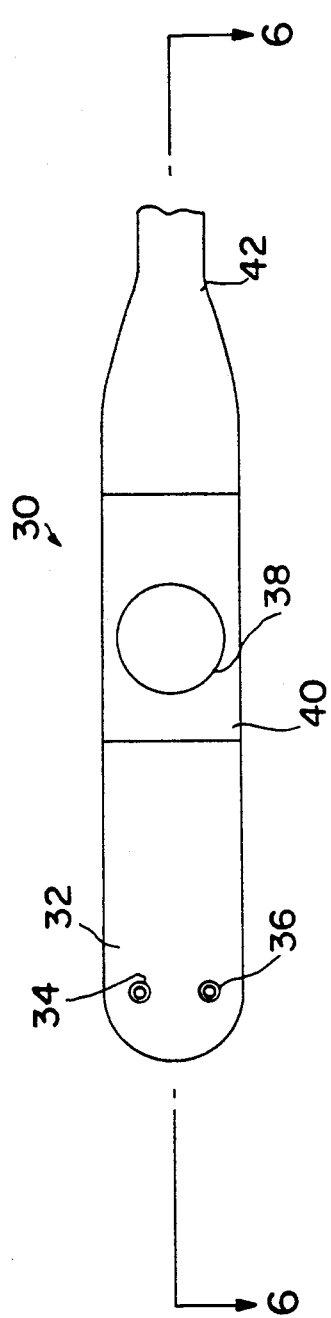
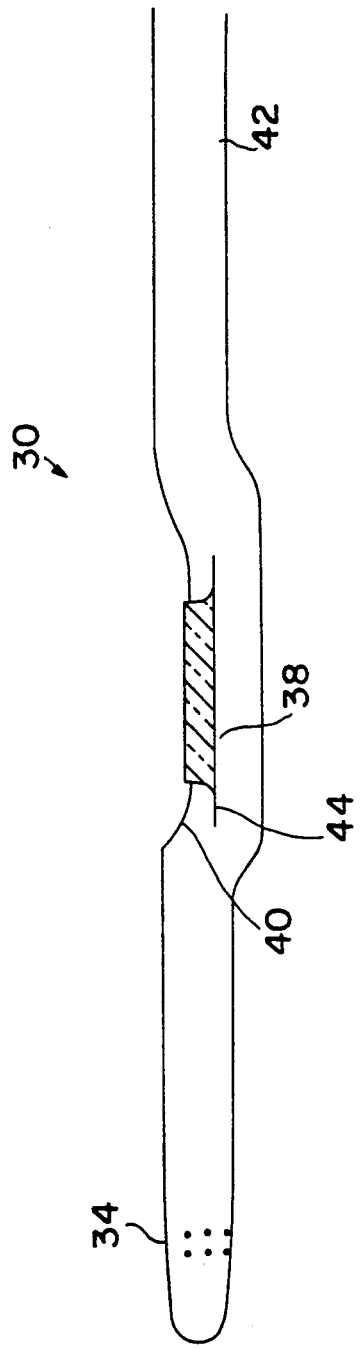

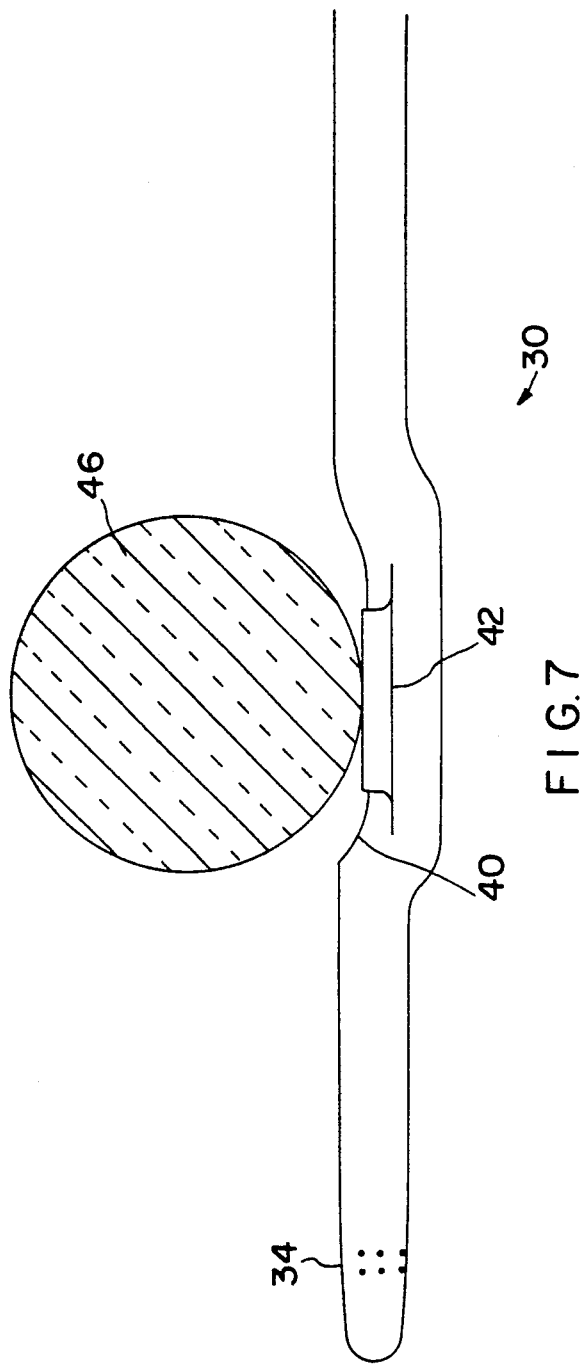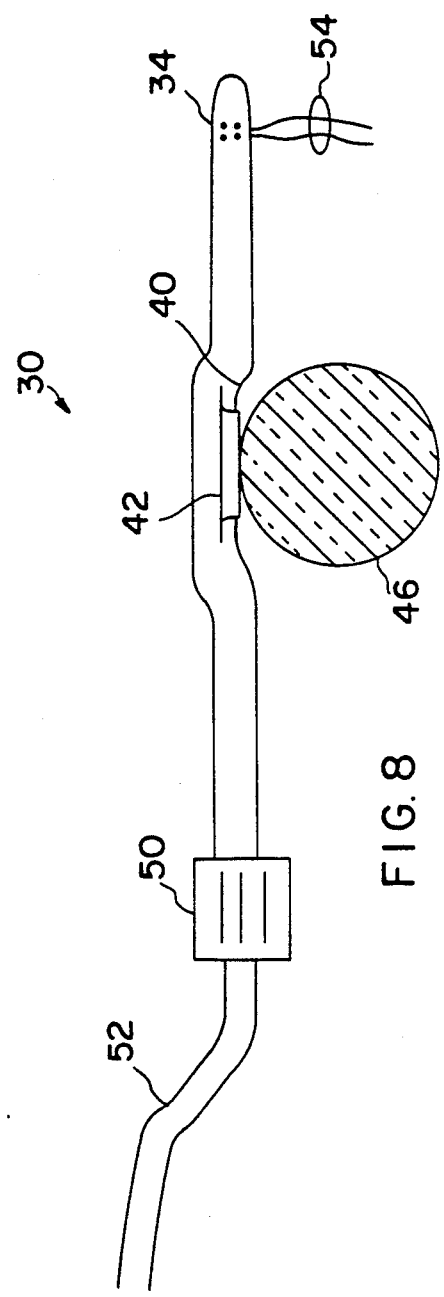

STEROID ELUTING ELECTRODE FOR PERIPHERAL NERVE STIMULATION

CROSS-REFERENCE TO COPENDING APPLICATIONS

This application is a continuation-in-part of copending U.S. Pat. No. 5,092,352, issued Mar. 3, 1992, entitled "Steroid Eluting Cuff Electrode for Peripheral Nerve Stimulation". It is related to U.S. Pat. No. 5,009,229, issued Apr. 23, 1991, entitled "Steroid Eluting Intramuscular Lead" which is assigned to the assignee of this application.

BACKGROUND OF THE INVENTION

1. Field of the Invention

The present invention generally relates to implantable medical devices and more particularly relates to electrodes for electrically coupling to nerve tissue.

2. Description of the Prior Art

The use of electrodes to monitor electrical activity and stimulate body tissue is quite old. U.S. Pat. No. 1,662,446 issued to R. H. Wappler teaches an early electrode system. The Wappler electrode is used for acute stimulation only, and is not implantable.

An early stimulation electrode which is chronically implantable is taught by S. I. Schwartz, et al in U.S. Pat. No. 3,421,511, herein incorporated by reference. U.S. Pat. No. 3,654,933 issued to Hagfors, herein incorporated by reference, teaches an improved stimulation electrode for chronic implantation. Clinical experience with the electrodes taught by Schwartz, et al and Hagfors may produce excess inflammation and irritation in certain applications. This inflammation and irritation results in swelling of the nerve tissue and ultimately an unacceptable increase in impedance and threshold of the nerve tissue/electrode interface.

U.S. Pat. No. 4,341,221 issued to Testerman, incorporated herein by reference, teaches an improved nerve electrode for chronic implantation which uses gel electrodes. While offering some improvement, excess irritation is yet experienced in some patients.

Cardiac pacing leads which sense and stimulate activity in the myocardial muscle tissue have been in use for some time. U.S. Pat. No. 4,711,251 issued to Stokes teaches an endocardial pacing lead having steroid drug embedded in the distal tip. U.S. Pat. Nos. 4,506,680; 4,577,642; and 4,606,118 teach similar endocardial pacing leads, all of which have an embedded steroid drug. U.S. Statutory Invention Registration No. H356 discloses a pacing lead suitable for epicardial application which elutes a steroid drug. Because cardiac pacing leads establish electrical contact with cardiac muscle tissue rather than nerve tissue, the total contact area is extremely small to increase current density. Therefore, the area of cardiac muscle tissue to be treated by the embedded drug is so small that only minute quantities of drug need be eluted.

U.S. Pat. No. 4,602,624 issued to Naples et al shows a cuff for implanting around a nerve. The reference shows separate embodiments which may dispense either electrical stimulation or a liquid medical agent.

SUMMARY OF THE INVENTION

The present invention overcomes the disadvantages of the prior art by directly treating the inflammation and irritation of the nerve tissue caused by contact with the electrode.

This area is treated with an anti-inflammatory drug such as a glucocortico steroid which is topically applied to the excitable nerve tissue at a predetermined chronic rate.

The steroid drug is embedded in a polymeric matrix which permits the drug to leach out at the desired rate. The polymeric matrix is a layer of material which is applied to the outer substrate of the electrode system. The metallic electrode elements are positioned on the polymeric matrix layer opposite the outer substrate.

In a first embodiment, the outer substrate is wrapped about the nerve at the desired location, and the edges of the outer substrate are sutured to hold the electrode in place. The metallic electrode elements contact the nerve tissue directly and are electrically coupled to an insulated lead which couples to remote electronic circuitry. The polymeric matrix thus treats the entire surface area of the nerve tissue which is wrapped with the cuff formed by the sutured outer substrate.

The outer substrate is shaped in the form of a half cuff in the electrode system of a second embodiment. The electrode element is a metallic disc which is recessed into the polymeric matrix containing the drug to be dispensed. The nerve to be contacted is placed within the recess of the substrate. The half cuff is sutured in place so as to position the recessed metallic disc in direct contact with the nerve tissue. Because the second embodiment does not encircle the nerve, inadvertent swelling of the nerve tissue does not cause immediate tissue damage. Electrode systems according to the second embodiment may be coupled to nerve tissue to provide sensing and/or stimulation of the nerve.

A further advantage of a half cuff geometry which does not completely encircle the nerve is present with the use of hydrophilic gels. As demonstrated in the above referenced U.S. Patent to Testerman, such gels can be effectively used as electrode surfaces. However, continued hydration causes the gel material to swell in volume. This tends to increase pressure on the nerve tissue using full cuff geometries. With the half cuff invention as taught herein, continued hydration of the gel does not add stress to the nerve tissue.

BRIEF DESCRIPTION OF THE DRAWINGS

Other objects of the present invention and many of the attendant advantages of the present invention will be readily appreciated as the same become better understood by reference to the following detailed description when considered in connection with the accompanying drawings, in which like reference numerals designate like parts throughout the figures thereof and wherein:

FIG. 5 is a top view of an alternate embodiment of the present invention.

FIG. 6 is a sectioned side view of the electrode of FIG. 5.

FIG. 7 is a side view of the electrode of FIG. 5 in contact with nerve tissue.

FIG. 8 is a side view of the electrode of FIG. 5 used applied in another fashion.

DETAILED DESCRIPTION OF THE PREFERRED EMBODIMENTS

Figure 1:
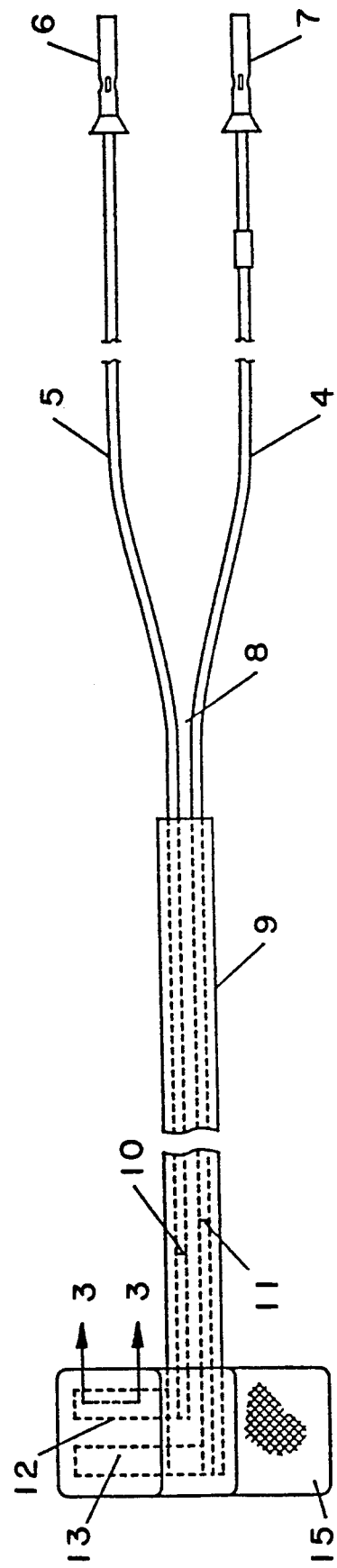
FIG. 1 is a plan view of a neurological lead suitable for chronic implantation incorporating the present invention.

FIG. 1 is a plan view of a neurological lead suitable for chronic implantation incorporating a first embodiment of the present invention. The proximal end of the lead has connector pins 6 and 7 which establish electrical contact with electronic circuitry remote from the site of the nerve. This electronic circuitry (not shown) may include sensing and monitoring functions and/or pulse generation functions for stimulation. Connector pins 6 and 7 are electrically coupled 10 to insulated wires 4 and 5 which join at point 8 and are covered distally by outer insulating sheath 9. The dashed lines show the location 10 and 11 of the extension of wires 4 and 5.

By way of illustration, outer substrate 15 is an insulator of a flexible polymeric material having a length of about ⅜ inch and a width of about ¼ inch. It is fixedly attached to outer insulating sheath 9. Attached to outer insulating sheath 9 is polymeric matrix layer 16 which is not shown in this illustration. The position of metallic foils 12 and 13 are shown by the dashed lines.

Figure 2:
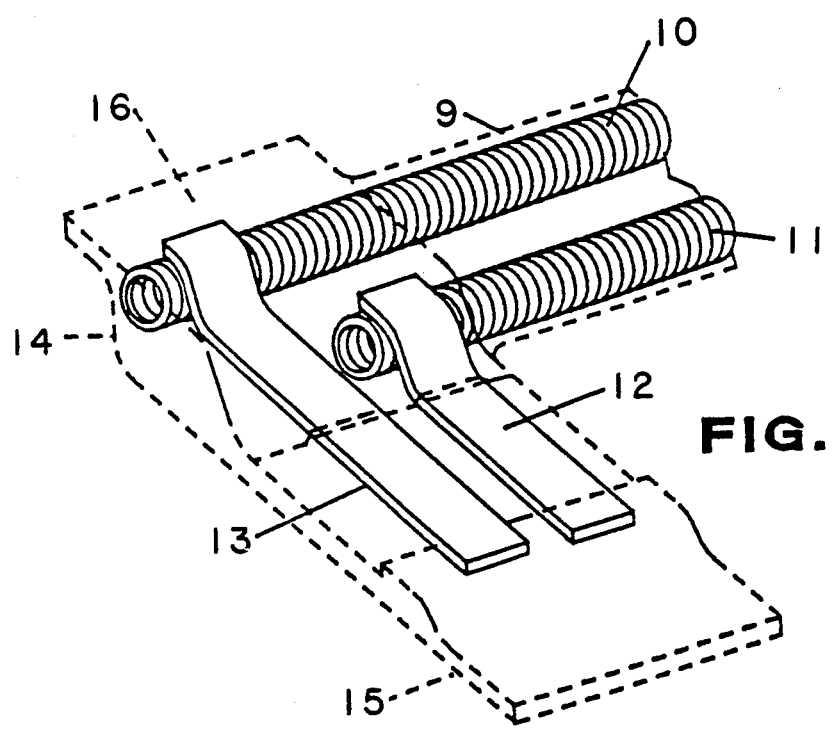
FIG. 2 is a closeup view of the electrode which contacts the nerve tissue.

FIG. 2 is a closeup view of the electrode structure of FIG. 1 as seen from the side which directly contacts the nerve tissue. Extension 10 is a conductor coil which is electrically coupled to metallic foil 13. Similarly, extension 11 is a conductor coil which is electrically coupled to metallic foil 12. Polymeric matrix layer 16 is shown as attached to the entire surface of outer substrate 15. Molded portion 14 of outer substrate 15, because of its increased thickness, tends to ensure ease of implantation by causing bending of outer substrate 15 at the desired points.

Polymeric matrix layer 16 may be fabricated in a variety of ways. By way of example and not to be deemed as limiting of the present invention, a preferred mode is a mixture of 0.2 milligrams of dexamethasone sodium phosphate with 0.5 cubic centimeters of silastic medical adhesive. The mixture is molded to the desired shape and allowed to cure. After curing, polymeric matrix layer 16 is fixedly attached to outer substrate 15 with silastic medical adhesive.

Figure 3:
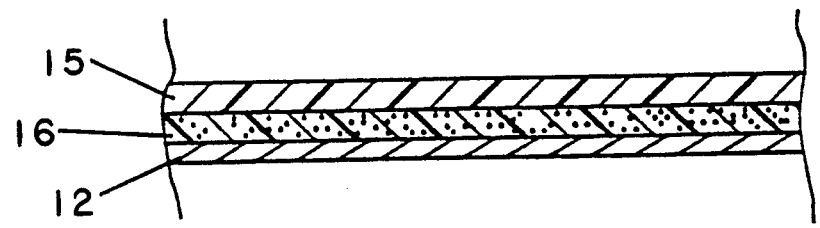
FIG. 3 is a closeup view of a crossection of the nerve electrode.

FIG. 3 is a closeup of a crossection of the electrode structure. Polymeric matrix layer 16 is attached to outer substrate 15. Metallic foil 12 is attached to polymeric matrix layer 16 using silastic medical adhesive. Metallic foil 13 (not shown) is similarly attached.

Figure 4:
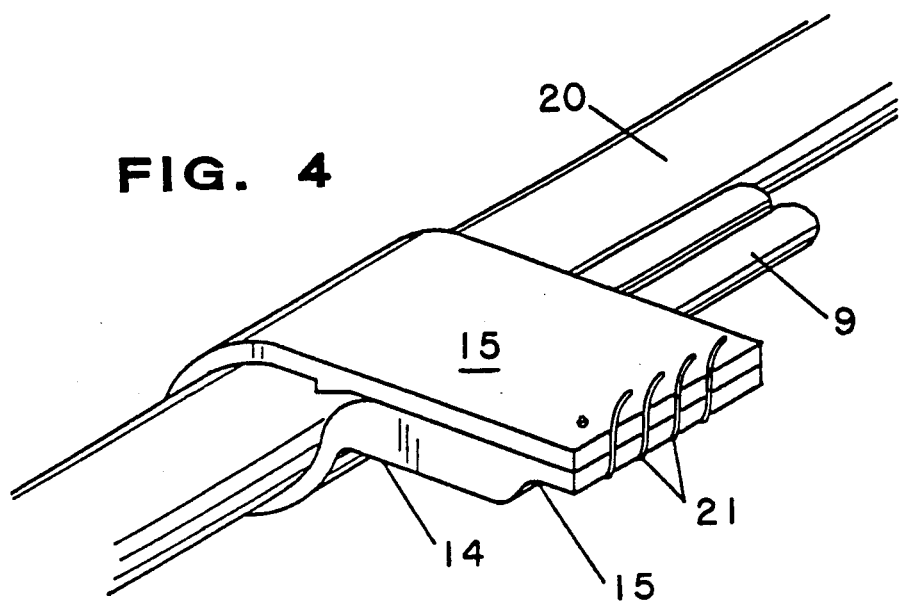
FIG. 4 is a view of the nerve electrode as sutured into place for chronic implantation about a nerve.

FIG. 4 is a view of the electrode assembly after it has been sutured into place for chronic implantation. Outer substrate 15 is wrapped about nerve 20 as shown. It is fixedly attached using sutures 21 at the edges of outer substrate 15. Molded portion 14 is shown as ensuring that outer substrate 15 is wrapped in the proper way. Outer insulating sheath 9 is shown as proceeding proximally from the electrode assembly parallel to nerve 20.

FIG. 5 is a top view of an alternative embodiment 30 of the present invention. It consists of a flexible substrate 32 of biocompatible, electrically insulative material, such as a suitable polymer, which may be reinforced with a polyester netting. The substrate has suture holes 34 and 36 by which it is fixedly held in position. The proximal end of substrate 32 is tapered to provide for molded attachment of an insulated lead (not shown). Substrate 32 contains trough 40 for fitting about the nerve. Approximately centered within trough 40 is recessed metallic disc 38 which is electrically coupled to the insulated lead. Metallic disc 38 provides electrical contact with the nerve tissue. An alternative to the use of metallic disc 38 is a conductive hydrophilic gel electrode as taught in the above referenced U.S. Patent to Testerman.

FIG. 6 is a sectioned side view of the alternative embodiment 30. Metallic disc 38 is maintained in position within substrate 32 by flange 44 within a corresponding groove of substrate 32. The active drug dispensing area of alternative embodiment 30 is located along the surface of trough 40.

An alternative approach is to locate a plug of steroid eluting drug within the body of the electrode by using an electrode of a porous material. The plug is the same material described previously, a polymeric matrix from which a drug such as dexamethasone is eluted. The drug passes from the matrix plug through the electrode and to the nerve tissue.

FIG. 7 is a side view of alternative embodiment 30 in electrical contact with nerve 46. The surface of trough 40 compresses slightly against nerve 46 to provide good mechanical contact. Nerve 46 is compressed against metallic disc 42 to provide the necessary electrical contact. An insulative lead (not shown) is coupled to metallic disc 42 as shown in the other embodiments.

FIG. 9 is a side view of alternative embodiment 30 in electrical contact with nerve 46 wherein the cuff electrode structure is inverted and placed over the nerve. Sutures 54 are used to fixedly attach the cuff in place. Also shown is insulated lead 52 which is electrically coupled to metallic disc 42 through strain relief coupling 50. All other referenced components are as previously described.

Having thus described the preferred embodiments of the present invention, those of skill in the art will be readily able to apply the present invention to yet other embodiments without departing from the scope of the claims which are hereto attached.

I claim:

1. An electrode for coupling to nerve tissue of a patient comprising:
   a. an insulating substrate for partially encircling said nerve tissue, said substrate comprising means for fixedly attaching said electrode to said patient;
   b. means coupled to said insulative substrate for establishing electrical contact with said nerve tissue; and
   c. means coupled to said insulative substrate for treating inflammation and irritation of said nerve tissue;
   wherein said insulative substrate is recessed to create a trough to accept said nerve tissue, said establishing means is coupled to said insulative substrate at said trough, and said establishing means comprises a metallic disc.

2. An electrode according to claim 1 wherein said metallic disc further comprises a flange coupled to said insulative substrate.

3. An electrode for coupling to nerve tissue of a patient comprising:
   a. an insulative substrate, said substrate comprising means for fixedly attaching said electrode to said patient;
   b. means coupled to said insulative substrate for establishing electrical contact with said nerve tissue, said establishing means comprising a porous conductor of electricity; and c. means located within said establishing means for treating inflammation and irritation of said nerve tissue;

wherein said insulative substrate is recessed to accept said nerve tissue, said establishing means is coupled to said insulative substrate at said recess, and said porous conductor of electricity is a metallic disc having an outer flange coupled to said insulative substrate.

* * * * *